(12) United States Patent
Wen

(10) Patent No.: US 12,390,151 B2
(45) Date of Patent: Aug. 19, 2025

(54) SYSTEM AND METHOD FOR DETECTION OF ONSET AND ICTAL PHASES OF AN EPILEPSY SEIZURE

(71) Applicant: SIPPLINK Technology Corporation, Hsinchu (TW)

(72) Inventor: Kuei Ann Wen, Hsinchu County (TW)

(73) Assignee: SIPPLINK TECHNOLOGY CORPORATION, Hsinchu (TW)

( * ) Notice: Subject to any disclaimer, the term of this patent is extended or adjusted under 35 U.S.C. 154(b) by 558 days.

(21) Appl. No.: 17/882,410

(22) Filed: Aug. 5, 2022

(65) Prior Publication Data

US 2023/0172528 A1 Jun. 8, 2023

(30) Foreign Application Priority Data

Dec. 7, 2021 (TW) .................. 110145762

(51) Int. Cl.
*A61B 5/00* (2006.01)
*A61B 5/11* (2006.01)

(52) U.S. Cl.
CPC .......... *A61B 5/4094* (2013.01); *A61B 5/0002* (2013.01); *A61B 5/11* (2013.01); *A61B 5/6898* (2013.01); *A61B 5/7475* (2013.01); *A61B 2562/0219* (2013.01); *A61B 2562/04* (2013.01)

(58) Field of Classification Search
CPC ........ A61B 5/4094; A61B 5/0002; A61B 5/11
See application file for complete search history.

(56) References Cited

U.S. PATENT DOCUMENTS

| | | | |
|---|---|---|---|
| 9,332,939 B2 | 5/2016 | Osorio | |
| 2011/0230730 A1* | 9/2011 | Quigg | A61B 5/386 600/301 |
| 2012/0197092 A1 | 8/2012 | Luo et al. | |
| 2013/0060167 A1* | 3/2013 | Dracup | G16H 80/00 600/595 |
| 2013/0131846 A1 | 5/2013 | Bulaj et al. | |
| 2015/0100643 A1* | 4/2015 | Pennanen | H04W 4/029 709/204 |
| 2017/0182362 A1* | 6/2017 | McLeod | A61B 5/0002 |
| 2018/0360368 A1 | 12/2018 | Gatto et al. | |
| 2019/0030396 A1* | 1/2019 | Karc | G06V 40/23 |
| 2020/0187845 A1* | 6/2020 | Nathan | A61B 5/681 |
| 2022/0265197 A1* | 8/2022 | Tan | A61B 5/11 |
| 2023/0341509 A1* | 10/2023 | Beg | G01S 13/765 |
| 2023/0386025 A1* | 11/2023 | Loddenkemper | A61B 5/1113 |

FOREIGN PATENT DOCUMENTS

WO WO2017184772 A 10/2017

* cited by examiner

*Primary Examiner* — Daniel L Cerioni
(74) *Attorney, Agent, or Firm* — Muncy, Geissler, Olds & Lowe, P.C.

(57) ABSTRACT

A system for detection of onset and ictal phases of an epileptic seizure comprises at least one motion sensor, at least one intermediate device and a sensing data interpretation device, embedded with an application program that, after execution, detects onset and ictal phases of an epileptic seizure, and configured to mark a feature or a reference on, or normalize sensing data of a motion sensing data file, wherein the reference comprises at least one of a phase of an epileptic seizure, a sensor position and a sensing time.

23 Claims, 14 Drawing Sheets

|  |  | Starting time (s) | period (s) |
|---|---|---|---|
| Tonic period | This invention | 18777 | 12.1 |
|  | Physician's judgment | 18777.29 | 15.68 |
|  | Error (absolute value) | 0.29 | 3.58 |
| Clonic phase | This invention | 18792.9 | 28.1 |
|  | Physician's judgment | 18792.97 | 28.18 |
|  | Error (absolute value) | 0.07 | 0.08 |
| Post-ictal | This invention | 18822 | 12.5 |
|  | Physician's judgment | 18821.15 | 13.08 |
|  | Error (absolute value) | 0.85 | 0.58 |

Fig. 4B

|  |  | Starting time (s) | period (s) |
|---|---|---|---|
| Tonic period | This invention | 18713.6 | 12 |
|  | Physician's judgment | 18777.29 | 15.68 |
|  | Error (absolute value) | 63.69 | 3.68 |
| Clonic phase | This invention | 18731 | 26.7 |
|  | Physician's judgment | 18792.97 | 28.18 |
|  | Error (absolute value) | 61.97 | 1.48 |
| Post-ictal | This invention | 18757.7 | 24.2 |
|  | Physician's judgment | 18821.15 | 13.08 |
|  | Error (absolute value) | 63.45 | 11.12 |

Fig. 3B

|  |  | Starting time (s) | period (s) |
|---|---|---|---|
| Tonic period | This invention | 18423.4 | 14.9 |
|  | Physician's judgment | 18777.29 | 15.68 |
|  | Error (absolute value) | 353.89 | 0.78 |
| Clonic phase | This invention | 18438.5 | 28 |
|  | Physician's judgment | 18792.97 | 28.18 |
|  | Error (absolute value) | 354.47 | 0.18 |
| Post-ictal | This invention | 18466.5 | 4.3 |
|  | Physician's judgment | 18821.15 | 13.08 |
|  | Error (absolute value) | 354.65 | 8.78 |

Fig. 6B

|  |  | Starting time (s) | period (s) |
|---|---|---|---|
| Tonic period | This invention | 18660.8 | 11.7 |
|  | Physician's judgment | 18777.29 | 15.68 |
|  | Error (absolute value) | 116.49 | 3.98 |
| Clonic phase | This invention | 18677.1 | 27.3 |
|  | Physician's judgment | 18792.97 | 28.18 |
|  | Error (absolute value) | 115.82 | 0.88 |
| Post-ictal | This invention | 18704.4 | 14.4 |
|  | Physician's judgment | 18821.15 | 13.08 |
|  | Error (absolute value) | 116.75 | 1.32 |

Fig. 5B

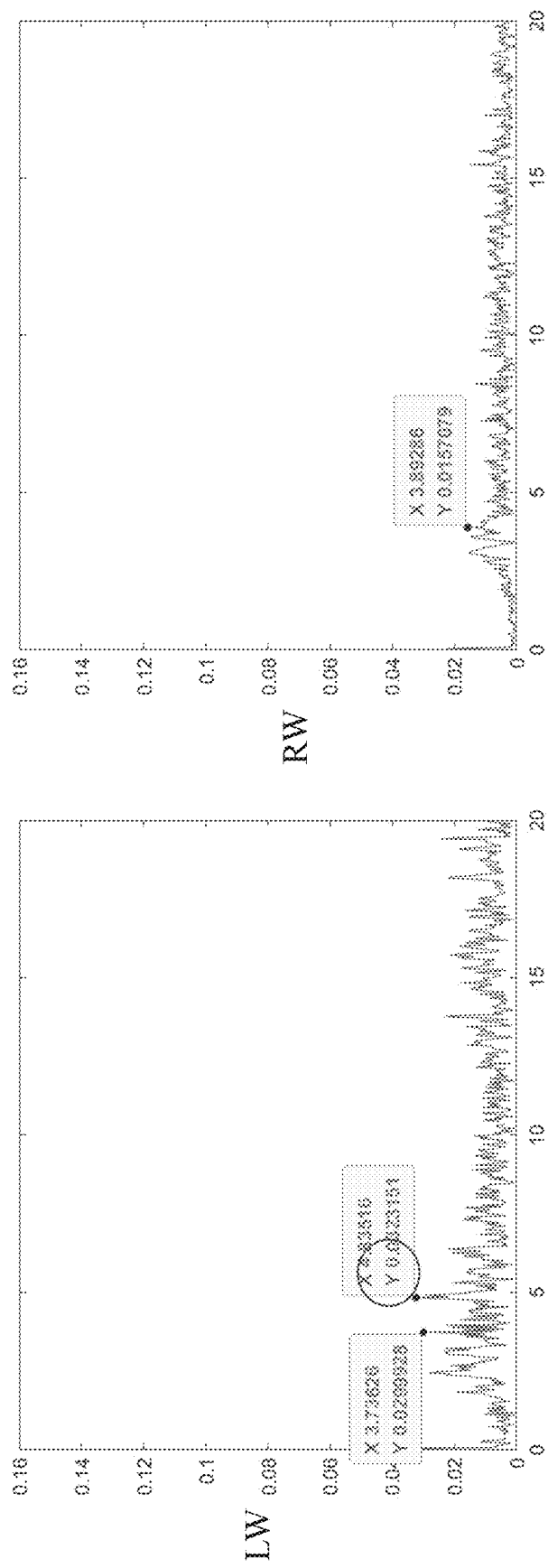

SYSTEM AND METHOD FOR DETECTION OF ONSET AND ICTAL PHASES OF AN EPILEPSY SEIZURE

TECHNICAL FIELD

The present invention relates to a system and method for detecting epileptic seizures and their history, and more particularly to a system and method for detecting epileptic seizures and their history using biomechanical evaluation technology.

BACKGROUND OF THE INVENTION

Epilepsy seizure, or epilepsy, is a fairly common cranial nerve disease. According to research statistics, about 5-10 out of every 1,000 people suffer from epilepsy, so Taiwan's existing epileptic population is about 100,000 to 200,000.

In order to assist physicians and professionals in the detection, diagnosis, evaluation, and treatment of epilepsy patients, the industry has developed a variety of epileptic seizures and history detection and recording devices. Traditional epileptic seizure and course detection devices mainly detect the brain waves of patients. This is an intuitive detection method, because it is generally believed that seizures are caused by abnormal discharge of a group of brain cells.

Techniques designed for studying and monitoring seizures have typically relied upon electroencephalography (EEG), which characterizes electrical signals using electrodes attached to the scalp or head region of a seizure-prone individual or seizure patient. In EEG, electrodes may be positioned so as to measure such activity; that is, electrical activity originating from neuronal tissue.

U.S. Pat. No. 9,332,939B2 discloses a "Detecting, quantifying, and/or classifying seizures using multimodal data" for detecting seizures through cardiac data (e.g., EKG) used in conjunction with motion data (e.g., accelerometer). Correct detection of seizures using less specific motion data is made possible, because the cardiac and motion data may be used to confirm each other. For example, tonic-clonic seizures are associated with losses of responsiveness and awareness, and falls to the ground if the patient is standing at onset. Common characteristics of movement include a "spike" in the inclinometer's output at seizure onset, a quiet period of accelerometer output after seizure onset, and a series of quasiperiodic "spikes" (at around 3 Hz) in accelerometer output after the tonic phase, followed by cessation of body movements, can be used to determine the entry of a tonic-clonic phase.

US2012197092 (A1) discloses dry sensor EEG/EMG and motion sensing system for seizure detection and monitoring that can measure a user's EEG/EMG and motor activity, automatically detect an epileptic seizure and perform actions, such as triggering an alarm and/or turning off the provoking stimulation. The invented system continuously monitors and stores a user's EEG/EMG and motor activity for doctor evaluation. The system can be mounted into/onto a pair of glasses (e.g., 3D glasses), and the user's eyes can be automatically covered by the glasses if a seizure is detected.

WO2017184772A1 discloses a "Systems and methods for characterization of seizures," using Electromyography (EMG) for seizure detection. In EMG, an electrode may be placed on or near the skin, over a muscle, to detect electrical activity resulting from muscle fiber activation. The inventor found that after filtering out low-frequency EMG signals, more accurate results can be obtained.

Patent publication US2013/131846 relates to a disease treatment game device, which can produce game images and sounds, and play games with disease treatment functions. The patient's actions are detected by motion sensors and provided to the game device; whereby corresponding screens are displayed.

US2018/360368A1 discloses a system and method for assessing and treating neurological deficits by analyzing voluntary and involuntary neuromuscular activity of a patient. The patient is required to perform certain prescribed physical and cognitive skills program to obtain data needed for remote assessment and treatment of the patient. The system uses a large number of detection devices, including different types of motion sensors and pressure sensors, to obtain the required data for the assessment.

From the observation of the existing technology, it can be found that there is a strong demand for the detection, monitoring, recording, judgment, ictal phases determination, etc. of epilepsy in the current society. Many researchers have also developed various devices and systems to meet the needs of professionals and patients. However, existing products usually need to use a variety of sensors and detectors. And invasive sensing devices are inevitable.

Therefore, the industry currently needs a novel system for detection of onset and ictal phases of an epileptic seizure that can use simple sensing devices to achieve correct epileptic history detection and recording.

At the same time, the industry also needs a system for detection of onset and ictal phases of an epileptic seizure that can be worn for a long time and continue to perform tasks such as detection, monitoring, recording, judgment, and determination.

Nevertheless, there is also a need for a system for detection of onset and ictal phases of an epileptic seizure that can collect seizure-related data belonging to multiple people for long-term monitoring, recording, diagnosis, and analysis.

OBJECTIVES OF THE INVENTION

The Objective of the present invention is to provide a novel system for detection of onset and ictal phases of an epileptic seizure that is simple in structure and easy to produce, and uses the basic sensing devices to generate useful information for epileptic history detection and recordation, and ictal phase determination.

Another objective of the present invention is also to provide a method for detection of onset and ictal phases of an epileptic seizure, applicable in a detection device that is simple in structure and easy to produce, and uses the basic sensing devices, whereby useful information for epileptic history detection and recordation, and ictal phase determination can be obtained and the ictal phases of an epileptic seizure can be correctly determined.

The system for detection of onset and ictal phases of an epileptic seizure according to the present invention comprises at least one motion sensor, at least one intermediate device and a sensing data interpretation device. The at least one motion sensor is communicatively connected to the sensing data interpretation device via at least one intermediate device. In some embodiments, the sensing data interpretation device can be embedded in the intermediate device, in particular, in the form of application software. The sensing data interpretation device can also be embedded in a server computer connected to the Internet in the form of application software.

The motion sensor comprises at least one three-axis inertial sensor for sensing the movement of the motion sensor and outputting the sensing data; an interface device for receiving user input for setting at least one format for output data of the motion sensor; a wireless communication device for establishing a communication channel with the at least one intermediate device for exchange of data; and a power supply for supplying electric power to the inertial sensor, the interface device and the wireless communication device. In a preferred embodiment of the present invention, the motion sensor is configured to continuously output the sensing data via the wireless communication device in the at least one format for a predetermined time.

In a preferred embodiment of the present invention, the motion sensor may further comprise a gyroscope and/or a three-axis magnetometer.

In a specific embodiment of the present invention, the motion sensor may further comprise a memory device for storage of the sensing data of the inertial sensor, the gyroscope and/or the magnetometer. In this embodiment, the motion sensor is configured to continuously store the sensing data in the memory device in the at least one format for a predetermined time.

The intermediate device may be a computer device equipped with a wireless communication function, preferably a smart phone, wherein a necessary application program is installed, to establish a communication channel with at least one of the plural motion sensors for exchange of data. The application program can also establish a communication channel with the sensing data interpretation device to exchange data. The intermediate device is configured to supply or transmit the sensing data sent by the at least one motion sensor to the sensing data interpretation device.

In a preferred embodiment of the present invention, the interface device of the motion sensor is built in the intermediate device. In this embodiment, the intermediate device is preferably configured to provide a setting interface, preferably a graphical setting interface, for the user to input setting parameters, and to send them to the motion sensor to change the settings of the motion sensor, such as the format of its output sensing data. In other embodiments of the present invention, the interface device of the motion sensor is built in the motion sensor.

The sensing data interpretation device is provided with a memory device for storing the sensing data generated by the at least one motion sensor. The sensing data interpretation device is provided with at least one application program for interpretation of the sensing data, each application program being configured to perform at least one of the following functions on the sensing data: marking a feature, marking reference, such as an ictal phase of an epileptic seizure, sensor position, sensing time; and normalization.

After the sensing data interpretation program is executed, it can mark a feature or a reference on a sensing data file. The feature to be marked can be at least one of the following features: the beginning and the end of an epileptic seizure; an ictal phase of the epileptic seizure, the transition of a phase of the epileptic seizure; or related descriptive information. Here, the term "phase" pertains to one of the phases of an epileptic seizure, including a preictal phase, onset, a tonic phase, a clonic phase and a postictal phase. The reference to be marked may include falling down, raising up etc.

After the sensing data interpretation program is executed, it can determine the sensing time for a sensing data file. After the sensing data interpretation program is executed, it can normalize the sensed values of a sensing data file.

The invented system for detection of onset and ictal phases of an epileptic seizure may also comprise a display device for retrieving one or more biomechanics data file from the memory device of the sensing data interpretation device according to a user's instruction, and displaying the requested information in a format and form specified by the user.

In such embodiments, the sensing data interpretation device is configured to recognize at least one synchronization feature in the one or more sensing data file, and determine for each file a start time and/or end time of displaying, as well as a timing of change of display content, including a data transition frequency and a frame change frequency along the time axis, according to the synchronization feature.

The sensing data interpretation device may be built in a server computer to form an epileptic seizure detection platform, which serves to communicate with a great number of motion sensors for uploading sensing data thereto via at least one intermediate device, and to communicate with computer devices in connection with the platform, for utilization of the sensing data stored therein, such as processing the sensing data and downloading various processing results.

The above and other objectives and advantages of the present invention can be more clearly appreciated from the following detailed description with reference to the accompanying drawings.

BRIEF DESCRIPTION OF THE DRAWINGS

FIG. 3B shows a comparison of the test result of FIG. 3A relative to the judgment of a physician.

FIG. 4B shows a comparison of the test result of FIG. 4A relative to the judgment of a physician.

FIG. 5B shows a comparison of the test result of FIG. 5A relative to the judgment of a physician.

FIG. 6B shows a comparison of the test result of FIG. 6A relative to the judgment of a physician.

FIGS. 8A-8D are waveform diagrams of the test results of an epileptic seizure, showing the 2-norm acceleration (ACC) of the measured tremor amplitude at the left ankle (FIG. 8A), right ankle (FIG. 8B), left wrist (FIG. 8C), and right wrist (FIG. 8D) of the patient of FIG. 7A-7D, after spectrum analysis, with the frequency as the horizontal axis. A circle in each figure marks the beginning of the clonic phase.

DETAILED DESCRIPTION OF THE INVENTION

Hereinafter, several preferred embodiments of the system and method for detection of onset and ictal phases of an epileptic seizure of the present invention will be described with reference to the drawings. It must be noted that, for the descriptions and illustrations of the embodiments of the present invention, the purpose is only to present the main features and possible implementation modes of the present invention in a brief manner. The scope of the present invention should extend to other embodiments that can be derived or deduced by the skilled persons in the industry.

Although there is no need to be bound or limited by any theory, the inventors have found that in the detection, monitoring, recording, judgment, and phase determination of epilepsy, the physician uses visual observations and rely on empirical judgment standards to provide diagnosis or suggestion. The main problem of this assessment method is, the standards used in the evaluation and diagnoses are not objective enough, because the evaluation and diagnoses mainly base on the experience of experts. The same action may get different evaluation results and suggestions. In addition, if the expert observes from a specific angle, the result may be biased. Even if it is video recorded from multiple angles and played synchronically, it is still not easy to observe the action correctly. Various high-tech instruments can be used to assist professionals in observation and diagnoses. But the instruments used so far are specially designed precision instruments, which are very expensive. At the same time, patients are required to insert probes and electrodes that invade the human body, or wear a large number of detection devices. This traditional epilepsy detection, monitoring, recording, judgment, and phase determination task is completely incompatible with the nature of epilepsy that occurs without warning.

The inventor found that a motion sensor made with the microelectromechanical technology is small in size and light in weight, and is suitable for wearing on the body to sense the activities of the body, if wireless communication capabilities are added thereon. Although the sensed results of the motion sensor are only readings and cannot be used to evaluate the motor activities or actions of a person, a suited interface can be provided to convert the readings of the motion sensor into data of a format that can be interpreted by an interpretation device, into useful healthcare or diagnoses information, or even into three-dimensional graphics describing the phases of an epileptic seizure, for assessment and suggestions by physicians.

Figure 1:
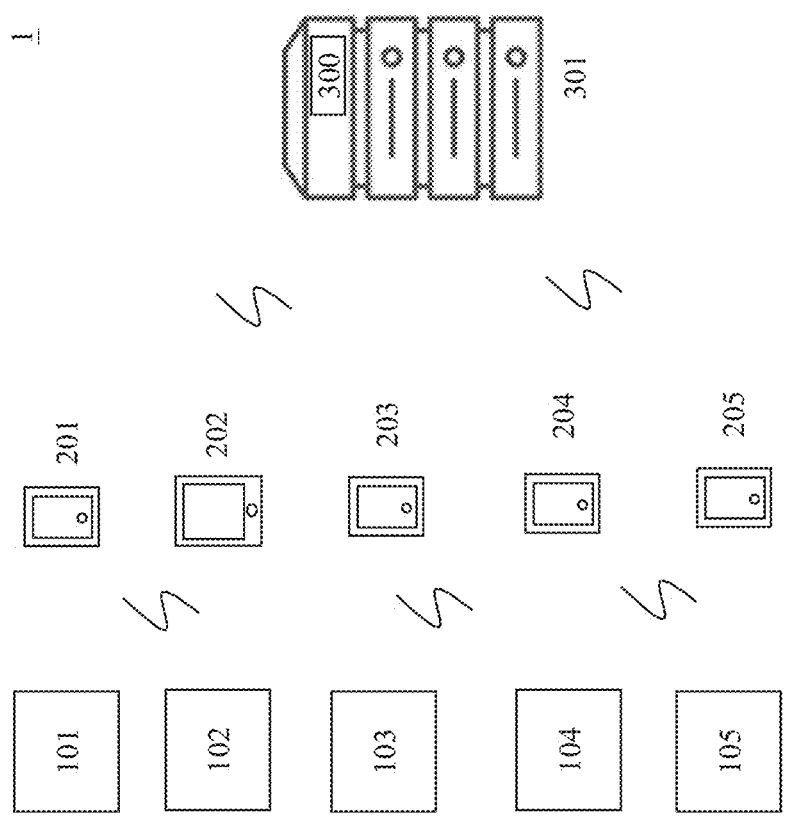
FIG. 1 is a system schematic diagram of an embodiment of the system for detection of onset and ictal phases of an epileptic seizure of the present invention.

Based on these discoveries, the present invention provides a system for detection of onset and ictal phases of an epileptic seizure, comprising at least one motion sensor, at least one intermediate device, and a sensing data interpretation device. FIG. 1 is a system schematic diagram showing an embodiment of the system for detection of onset and ictal phases of an epileptic seizure of the present invention. As shown in the figure, the system for detection of onset and ictal phases of an epileptic seizure 1 includes a plurality of motion sensors 101-105, a plurality of intermediate devices 201-205, and a sensing data interpretation device 300. Among them, each motion sensor 101-105 are communicatively connected to the sensing data interpretation device 300 via any one intermediate device 201-205. In some embodiments, the sensing data interpretation device 300 can be embedded in any of the intermediate devices 201-205, preferably in the form of application software. However, in the preferred embodiments of the present invention, the sensing data interpretation device 300 is embedded in a server computer 310 connected to the Internet, in the form of application software.

In such preferred embodiments, the sensing data interpretation device 300 can communicate with a great number of intermediate devices 201-205 and each intermediate devices 201-205 corresponds to one or more motion sensors 101-105. Each intermediate device 201-205 and the motion sensors 101-105 corresponding to the intermediate device, and the sensing data interpretation device 300, form a system for detection of onset and ictal phases of an epileptic seizure. As a result, the server computer can provide services for a great number of systems for detection of onset and ictal phases of an epileptic seizure; the whole system forms a platform for detection of onset and ictal phases of an epileptic seizure.

Figure 2:
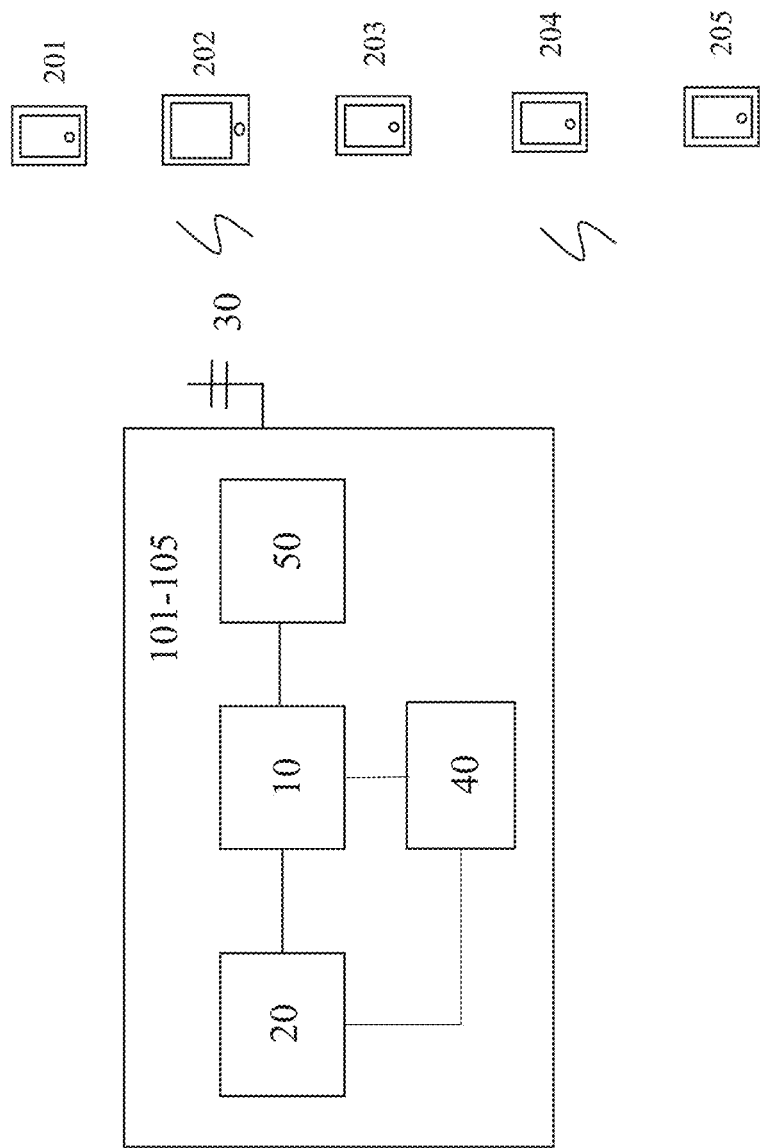
FIG. 2 is a block diagram of a motion sensor applicable to the present invention.

FIG. 2 is the block diagram of one embodiment of a motion sensor 101-105 applicable to the system for detection of onset and ictal phases of an epileptic seizure 1 of the present invention. The motion sensor 101 as shown in the figure includes a motion sensing element 10. The motion sensing element 10 is preferably a three-axis inertial sensor, and more preferably includes at least one of a three-axis accelerometer, a three-axis gyroscope, and a three-axis magnetometer. Preferably, it has a three-axis accelerometer and a three-axis gyroscope, or a three-axis accelerometer and a three-axis magnetometer. The accelerometer senses the motions of the motion sensor itself, and outputs the sensed value of their three-axial components. The gyroscope measures the angular velocity of the motions in the three-dimensional space and calculates the angular velocity. The magnetometer measures the geomagnetism and outputs the three-axial components of the sensed value. In most applications, only a three-axis accelerometer would be sufficient. However, as the motion sensor has become a popular commodity, motion sensing components available in the market have already provided a three-axis accelerometer, a gyroscope, and a three-axis magnetometer. Such motion sensing elements are very suitable for applications in the present invention. Of course, the motion sensing element 10 applicable to the present invention is not limited to this.

The motion sensor 101 also includes an interface device 20, for accepting user input and setting a predetermined format for the output data of the motion sensor 101. The interface device 20 is preferably a graphical interface for the user to input parameters to set the type and format of the output sensing data of the motion sensor 101. The interface device 20 is connected to a storage device or a temporary storage device (to be described in detail hereinafter) for storing or temporarily storing the sensing data of the motion sensing element 10, so to use the parameter input by the user to determine a type and/or a format of the output data of the storage device or the temporarily storage device. Here, the term "type" denotes to, for example, the particular axis of an axial component of the sensing data, such as, the X-axis component of the sensing data of the accelerometer. The term "format" denotes to, for example, the sampling frequency or time resolution of the output data.

As will be explained below, the interface device 20 does not necessarily have to be built in the motion sensor 101. In a preferred embodiment of the present invention, the interface device 20 of the motion sensor 101 is built in one of the intermediate devices 201-205 in the form of application software. In this embodiment, the intermediate device is configured to provide the setting interface, preferably a graphical human-machine interface, for ease of operation. The setting result is then provided to the motion sensor 101-105 in a wired or wireless manner.

The motion sensor 101 also has a wireless communication device 30 for establishing a communication channel with one of the plurality of intermediate devices 201-205 to exchange data. The wireless communication device 30 can be any small or micro wireless communication device, as long as it can communicate efficiently with the intermediate device 201-205, in particular, transmit the sensing data to the intermediate devices 201-205. As explained below, the intermediate devices 201-205 are preferably smart phones. In this embodiment, the motion sensors 101-105 only need to have short-distance wireless communication capabilities. In most embodiments of the present invention, the motion sensors 101-105 communicate with the intermediate devices 201-205 via Bluetooth wireless communication channels.

According to the present invention, most motion sensors 101-105 included in the system for detection of onset and ictal phases of an epileptic seizure 1 send the sensing data to the sensing data interpretation device 300 through the plurality of intermediate devices 201-205, without modifications, so that all processing and interpretation of the sensing data are performed in the sensing data interpretation device 300. Preferably, a plurality of motion sensors 101-105 corresponds to one intermediate device 201-205, and the intermediate device performs all communication and data exchange with the sensing data interpretation device 300. In this way, one intermediate device and a plurality of motion sensors 101-105 are combined into a group, to be used by a specific group of people, such as a group of a physician and several patients, one coach and specific athletes, etc. The sensing data interpretation device 300 can usually be built in the cloud, and through the support of the intermediate devices 201-205, the sensing data are sent to the sensing data interpretation device 300 for interpretation. In this way, the motion sensors 101-105 only need to be general-purpose motion sensors, and do not need to be equipped with specific functions. They can be used to perform various biomechanical monitoring and assessments, and provide descriptive information, for training, diagnosis and treatment. In such embodiments, the sensing data interpretation device can be embedded in one server computer and connected to the at least one intermediate device via Internet communication.

In addition, the motion sensor 101 also has a power supply 40. The power supply 40 supplies electric power to the motion sensing element 10, the interface device 20 and the wireless communication device 30. Any power supply device can be used as the power supply 40 of the present invention. The power supply 40 may be a household power source but is preferably a battery, for making the wearer feel comfortable. The power supply 40 may include a power management chip to save power and avoid accidents.

In a preferred embodiment of the present invention, the motion sensor 101 is configured to continuously output the reading value of the motion sensing element 10 via the wireless communication device 30 in a predetermined format for a predetermined time. Although it is broadcast in form, the sensed value is provided to one specific intermediate device, only.

In other embodiments of the present invention, the motion sensor 101 may further comprise a memory device 50 for storing the reading value of the motion sensing element 10. In this embodiment, the motion sensor 101 is configured to continuously store the reading value of the motion sensing element 10 in the memory device 50 in the preset format within the predetermined time.

The intermediate devices 201-205 are a computer equipped with wireless communication capabilities, usually a smart phone or a tablet computer. Of course, the intermediate device 201-205 can also be a computer with a special specification, equipped with necessary wireless communication function, to read or receive the sensed value from a specific group of motion sensors 101-105, and to send the sensing data to the sensing data interpretation device 300. A smart phone is preferable, because in addition to the above-mentioned capabilities, application software for various purposes can be built in the smart phone. However, the intermediate devices suitable for the present invention are not limited to smart phones and tablet computers.

Each of the intermediate devices 201-205 is embedded with a necessary application program, for establishing a communication channel with at least one of the plurality of motion sensors 101-105, for exchange of data. The main purpose of the application programs is to read, extract or receive sensing data from the motion sensors 101-105. The application program also provides a parameter setting function, to provide the control parameters set by the user to the motion sensors 101-105. The application program can also establish a communication channel with the sensing data interpretation device 300, also for exchange of data. The application program enables an intermediate devices 201-205 to communicate with the sensing data interpretation device 300, so to supply or transmit the sensing data sent by at least one of the plurality of sensing data of the sensing devices 101-105 to the sensing data interpretation device 300.

As mentioned above, the interface device 20 of the motion sensor can also be built in the intermediate device 201-205. The advantage of this embodiment is that the human-machine interface of the motion sensor 101-105 can be simplified, or even omitted. Other advantages include the ability to provide a graphical parameter-setting interface on, for example, the screen of a mobile phone, which facilitates the user to input setting parameters. Since both the motion sensor and the intermediate device have wireless communication capabilities, the set parameters are easily transmitted to the motion sensors 101-105 to set the type and the format of the output sensing data. The graphical human-machine interface can also provide the function of displaying the sensing data, so that setting of the parameters and display of the sensing data can be performed on the same interface device.

In addition, also as mentioned above, in a specific embodiment of the present invention, at least one motion sensor 101-105 may also be built in one of the intermediate devices 201-205. In particular, most mobile phones are equipped with useful motion sensing components. The sensing ability of the motion sensing components may be good enough for certain biomechanical assessment tasks. Although such embodiment falls within the scope of the present invention, the stand-along motion sensors are preferred, mainly because they are small-sized, lightweight and do not interfere with normal activities. The sensed results of the motion sensors are provided to the sensing data interpretation device 300 through an intermediate device, although in some embodiments, the sensing data interpretation device 300 may also be built in the intermediate device.

In most embodiments of this invention, the sensing data interpretation device 300 is installed in a server computer, so it can be equipped with powerful computing and memory capabilities. The memory device of the sensing data interpretation device 300 can store sensing data/information generated by a large amount of motion sensor. For example, to store the epileptic seizure monitoring data of 20,000 people generated in a year, 500 TB of memory capacity may be required. This capacity can be built in a small to medium enterprise server. The sensing data interpretation device 300 can build a variety of sensing data interpretation programs, each providing at least one interpretation function when in operation, and is configured to perform respective interpretation on the received/stored sensing data.

According to the system for detection of onset and ictal phases of an epileptic seizure of the present invention, the sensing data interpretation device 300 may automatically mark a feature or a reference, or normalize the sensing data received or stored in the memory device 301. The feature to be marked can be at least one of the following features: the beginning and the end of an epileptic seizure; type of the epileptic seizure, an ictal phase of the epileptic seizure, the transition of a phase of the epileptic seizure; or related descriptive information. Here, the term "phase" pertains to one of the phases of an epileptic seizure, including a preictal phase, onset, a tonic phase, a clonic phase and a postictal phase. It can also mark a sensor position, sensing time etc. on a sensing data file. The reference to be marked may include falling down, raising up etc.

In the following several embodiments of the epileptic seizure detection functions of the system for detection of onset and ictal phases of an epileptic seizure will be described, followed by introducing certain applications of the present invention.

Embodiment 1: Start Time and End Time of an Epileptic Seizure

Figure 3A:
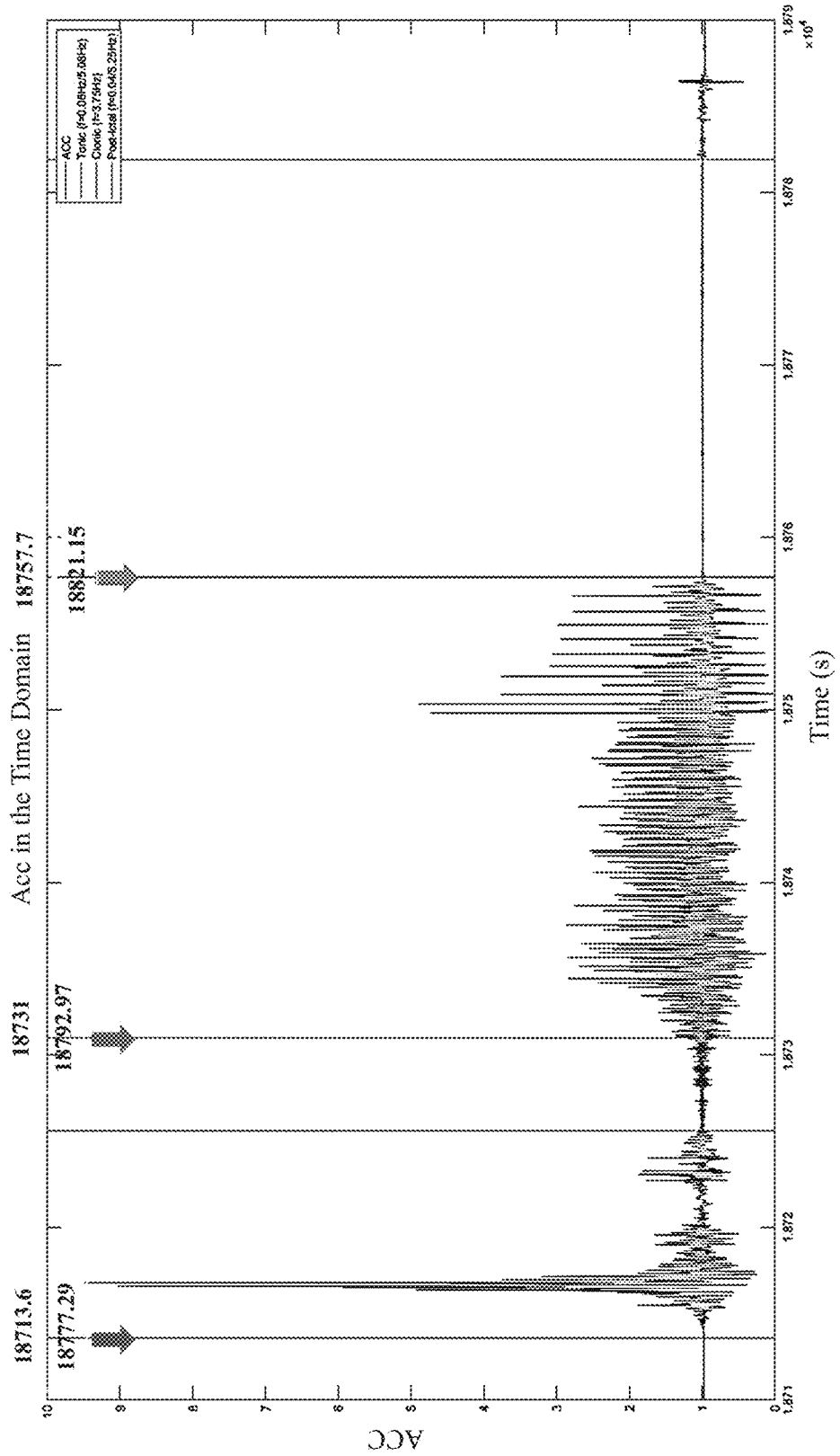
FIG. 3A is a waveform diagram of sensing data showing phases of an epileptic seizure. Shown in this figure are the sensor readings along the time axis of the tremor amplitude of the right ankle of a patient.

FIG. 3A is a waveform diagram of sensing data showing phases of an epileptic seizure. Shown in this figure are the sensor readings along the time axis of the tremor amplitude of the right ankle of a patient. During the measurement, the motion sensor is placed flat on the outer side of the patient's right ankle, and the sole of the patient's foot is in contact with the ground. As the waveform of the sensed result clearly shows the phases of an epileptic seizure, it is possible to write a computer program to determine the beginning, transition and end time points of the phases of an epileptic seizure, namely tonic, clonic and postictal, using the pattern recognition technology. The start time of the determination result is shown in the upper box in the figure. The number in the lower box in the figure is the start time determined by a physician. FIG. 3B shows a comparison of the test result of FIG. 3A relative to the judgment of a physician. As shown in the figure, the result of the judgment made by the pattern recognition method is close to that of the physician. It is proved that the start, transition and end times of the subject's actions can be easily identified, by simply wearing a motion sensor.

Figure 4A:
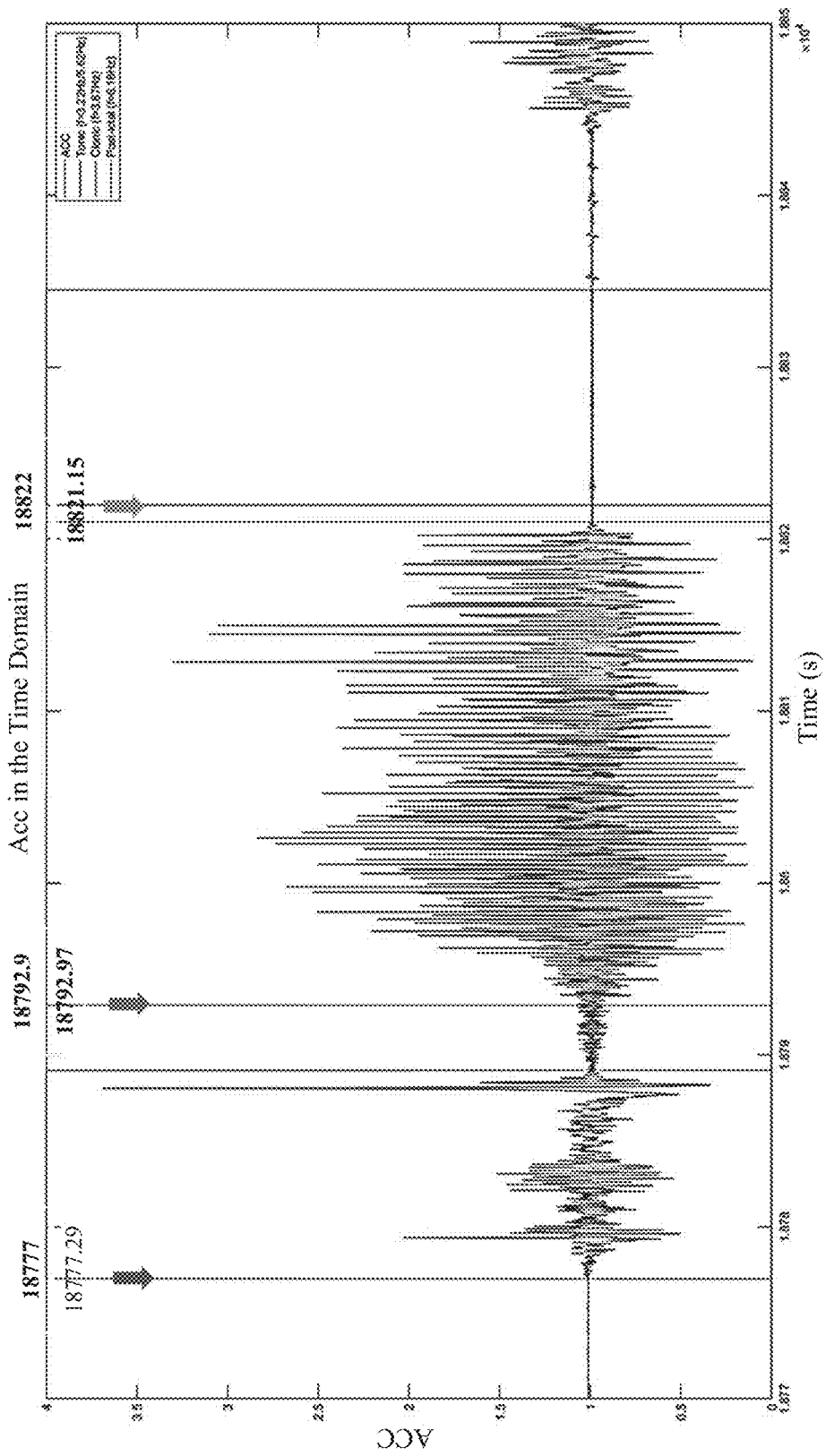
FIG. 4A is a waveform diagram of sensing data showing phases of an epileptic seizure, showing the sensor readings along the time axis of the tremor amplitude of the left ankle of a patient.
Figure 5A:
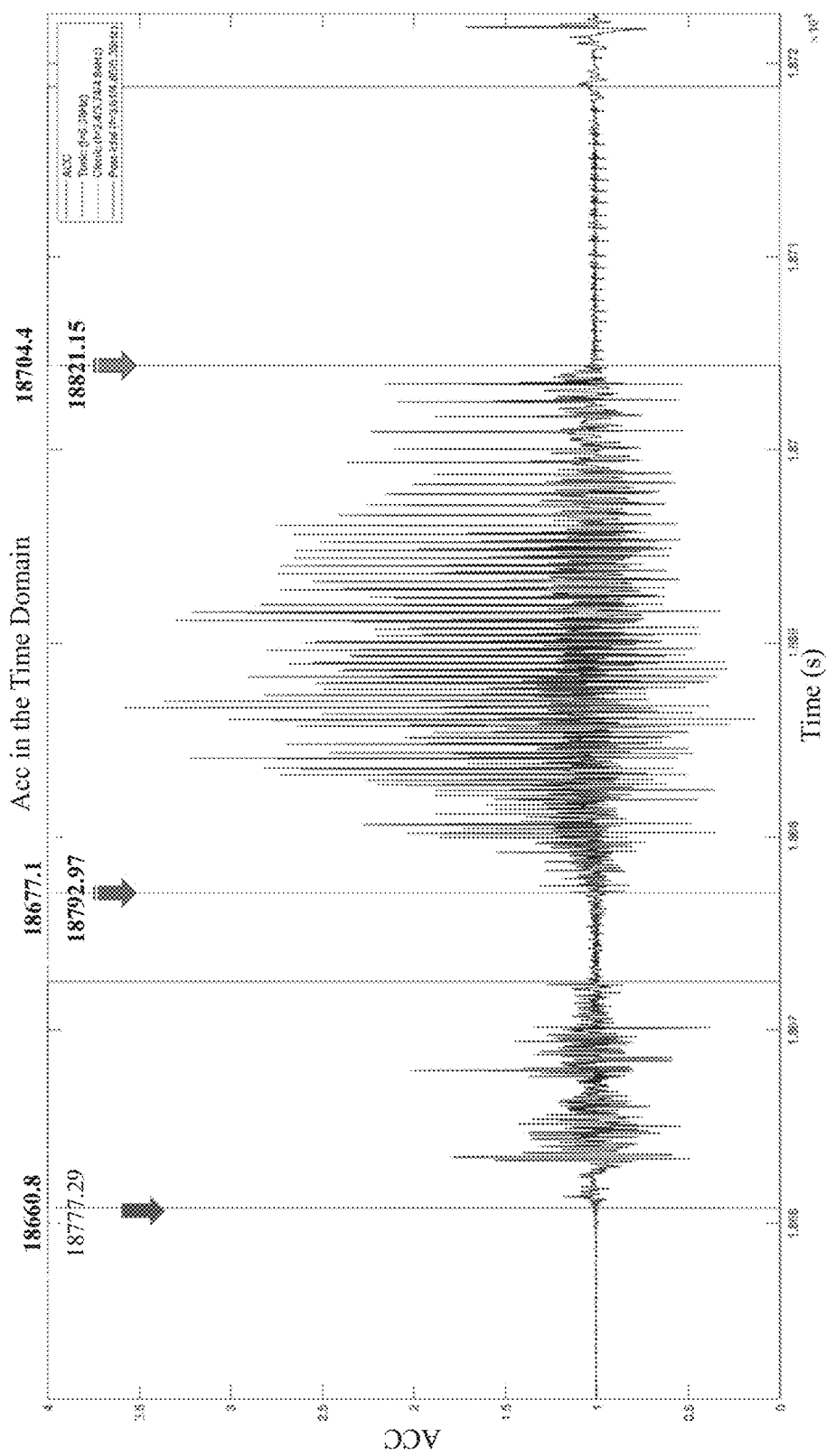
FIG. 5A is a waveform diagram of sensing data showing phases of an epileptic seizure. Shown in this figure are the sensor readings along the time axis of the tremor amplitude of the right wrist of a patient.
Figure 6A:
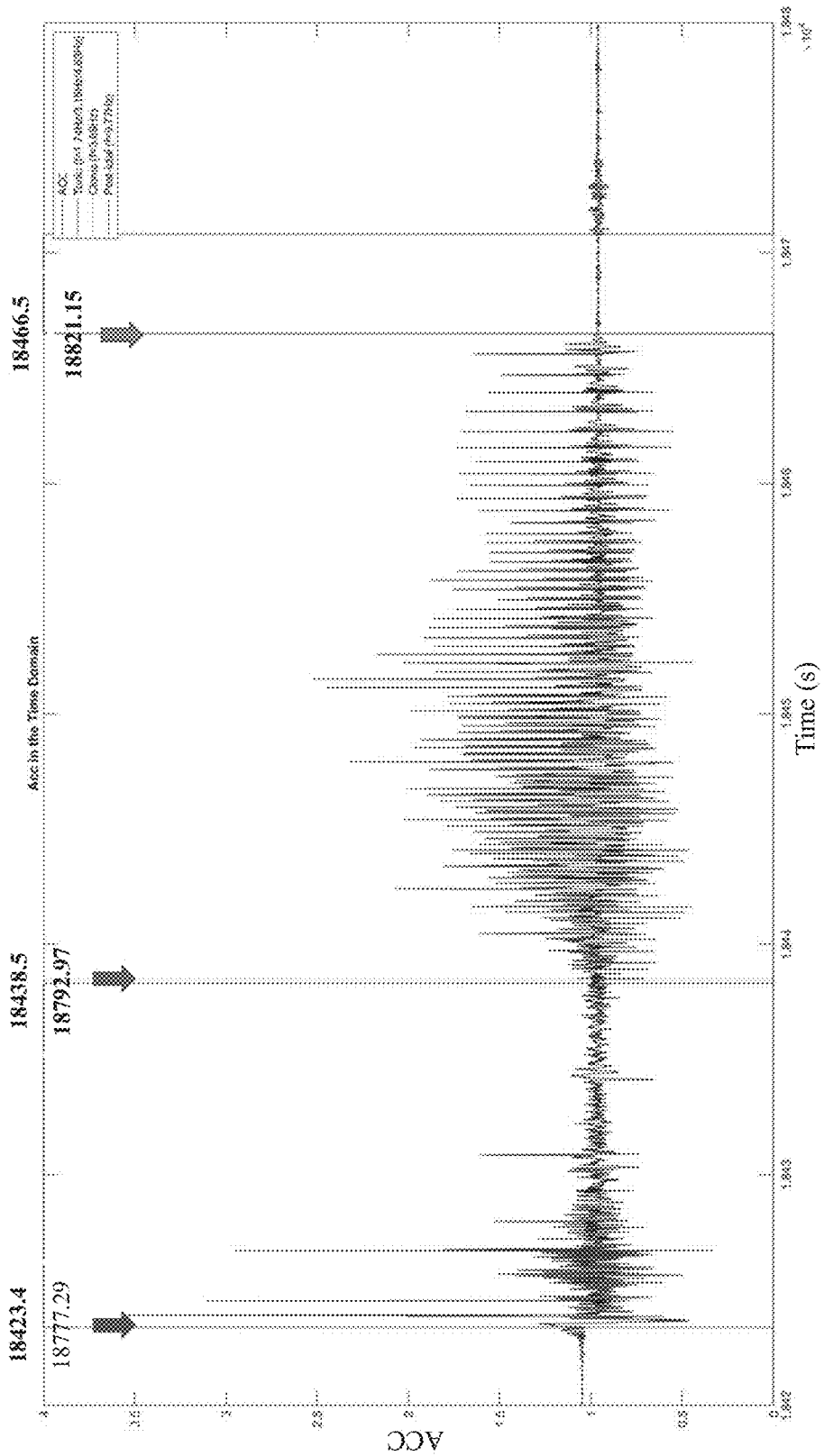
FIG. 6A is a waveform diagram of sensing data showing phases of an epileptic seizure, showing the sensor readings along the time axis of the tremor amplitude of the left wrist of a patient.
Figures 7A, 7B:
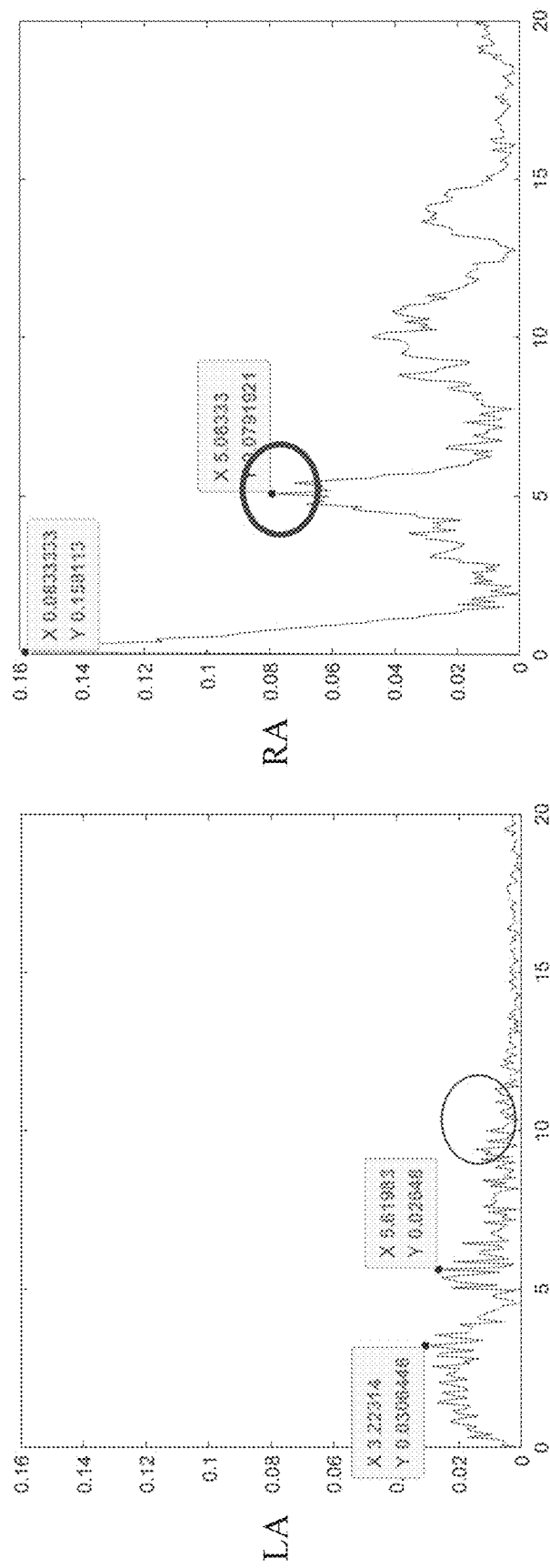
FIGS. 7A-7D are waveform diagrams of the test results of an epileptic seizure, showing the 2-norm acceleration (hereinafter "ACC," formula to be described below) of the measured tremor amplitude at the left ankle (FIG. 7A), right ankle (FIG. 7B), left wrist (FIG. 7C), and right wrist (FIG. 7D) of a patient, after spectrum analysis, with the frequency as the horizontal axis. A circle in each figure marks the beginning of the tonic phase.
Figures 7C, 7D:
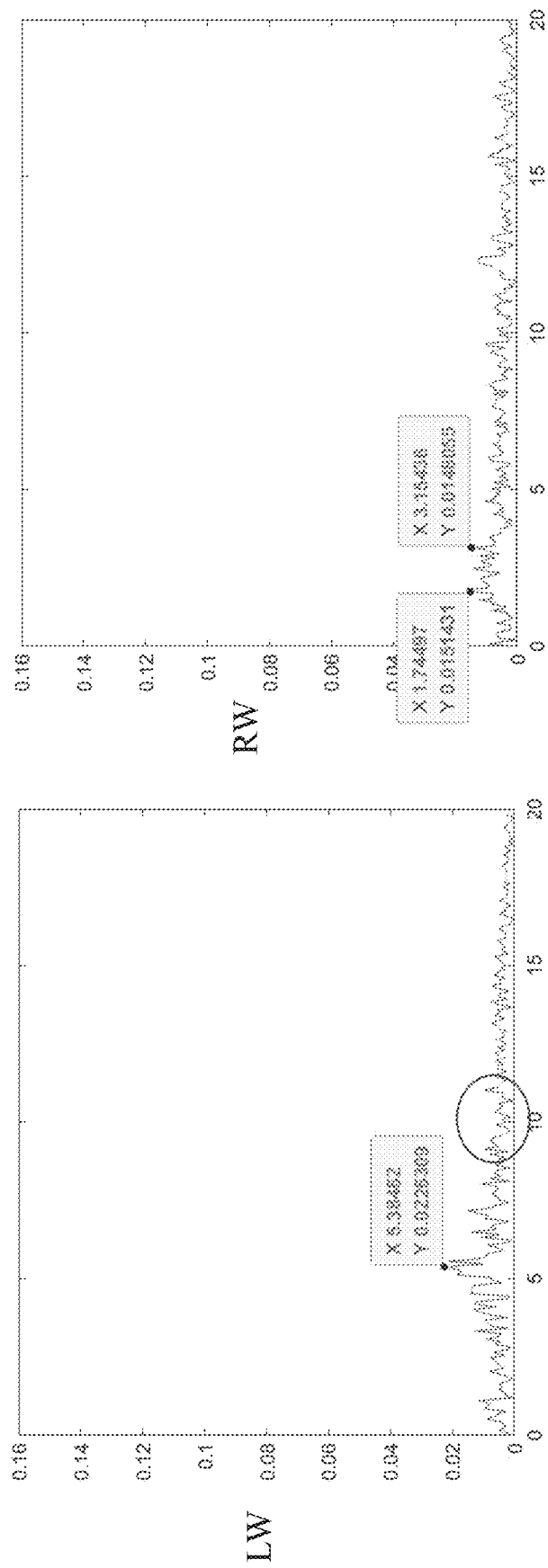
Figure 8B:
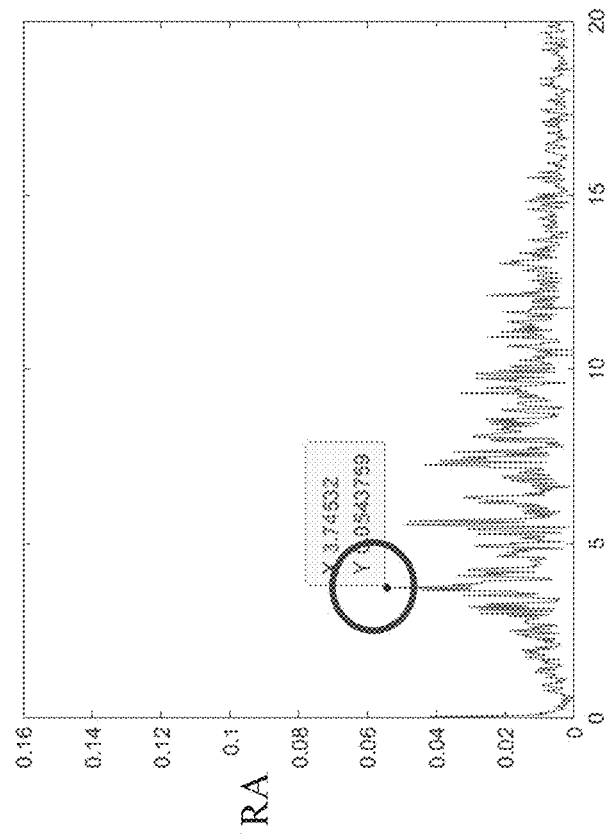
Figure 8A:
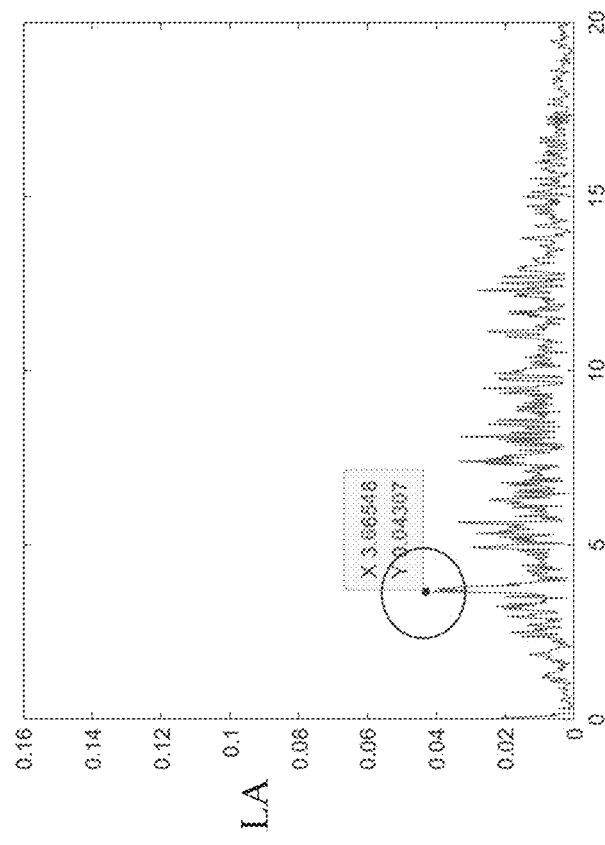

FIG. 4A is a waveform diagram of sensing data showing phases of an epileptic seizure, showing the sensor readings along the time axis of the tremor amplitude of the left ankle of the patient of FIG. 3A. FIG. 4B shows a comparison of the test result of FIG. 4A relative to the judgment of a physician. FIG. 5A is a waveform diagram of sensing data showing phases of an epileptic seizure, showing the sensor readings along the time axis of the tremor amplitude of the right wrist of the same patient. FIG. 5B shows a comparison of the test result of FIG. 5A relative to the judgment of a physician. In addition, FIG. 6A is a waveform diagram of sensing data showing phases of an epileptic seizure, showing the sensor readings along the time axis of the tremor amplitude of the left wrist of the patient. FIG. 6B shows a comparison of the test result of FIG. 6A relative to the judgment of a physician.

As shown in these figures, the judgment result made by the pattern recognition method based on the amplitude waveform is close to the judgment result of the physician. Although the absolute values of the errors in FIG. 5A and FIG. 6A are great, there is no substantial difference between them. Using other identification methods, correcting the pattern identification method, or correcting the identification result by, for example, adding an offset, the judgment result would be improved. It is proved that simply wearing a motion sensing device on the human body, the measured data can be used to determine the start, transition and end time of the phases of an epileptic seizure.

Experiment 2: Transition of the Epileptic Seizure Phase

FIGS. 7A-7D are waveform diagrams of the test results of an epileptic seizure, showing the 2-norm acceleration (ACC) of the measured tremor amplitude at the left ankle (FIG. 4A), right ankle (FIG. 4B), left wrist (FIG. 4C), and right wrist (FIG. 4D) of a patient, after spectrum analysis, with the frequency as the horizontal axis. During the test, the biomechanical sensing device is placed on the patient's ankle and wrist to record the patient's movement during admission.

$$ACC=\sqrt{accx^2+accy^2+accz^2}$$

As shown in the figures, after the frequency analysis, the results show the tonic phase can be roughly regarded as a signal component of 4.5-6 Hz, especially around 5 Hz. At this time point, the maximum ACC amplitude of the right ankle is RA, 0.079 but the frequency of the right wrist shows more recent noise. The ACC amplitude needs to be integrated twice to obtain the swing distance.

FIGS. 8A-8D are waveform diagrams of the test results of an epileptic seizure, showing the ACC value of the measured tremor amplitude at the left ankle (FIG. 8A), right ankle (FIG. 8B), left wrist (FIG. 8C), and right wrist (FIG. 8D) of the patient of FIG. 7A-7D, after spectrum analysis, with the frequency as the horizontal axis. A circle in each figure marks the beginning of the clonic phase. As shown in the figures, the clonic phase can be roughly regarded as a signal component of 3-4 Hz, when the maximum ACC amplitude of the right ankle is RA, 0.54.

The above experiments show that the seizure and its history can be judged only based on the sensing result of the motion sensing device. The ACC value is of great importance in providing information useful for judgment.

From the above experiments, it is known that the system for detection of onset and ictal phases of an epileptic seizure of the present invention can use a simple motion sensing element, especially very basic general-purpose motion sensors, worn on the patient's body, preferably on the extremities, such as wrists and ankles. The sensing data generated before, during and after the seizures, can produce significant features after appropriate calculations, and the features are useful in determining the start, transition and end times of the respective phases of an epileptic seizure. The obtained information does not only describe the history of the epileptic seizure but also provide useful references for physicians and experts for epilepsy detection, monitoring, recording, judgment, and phase determination.

Figure 9:
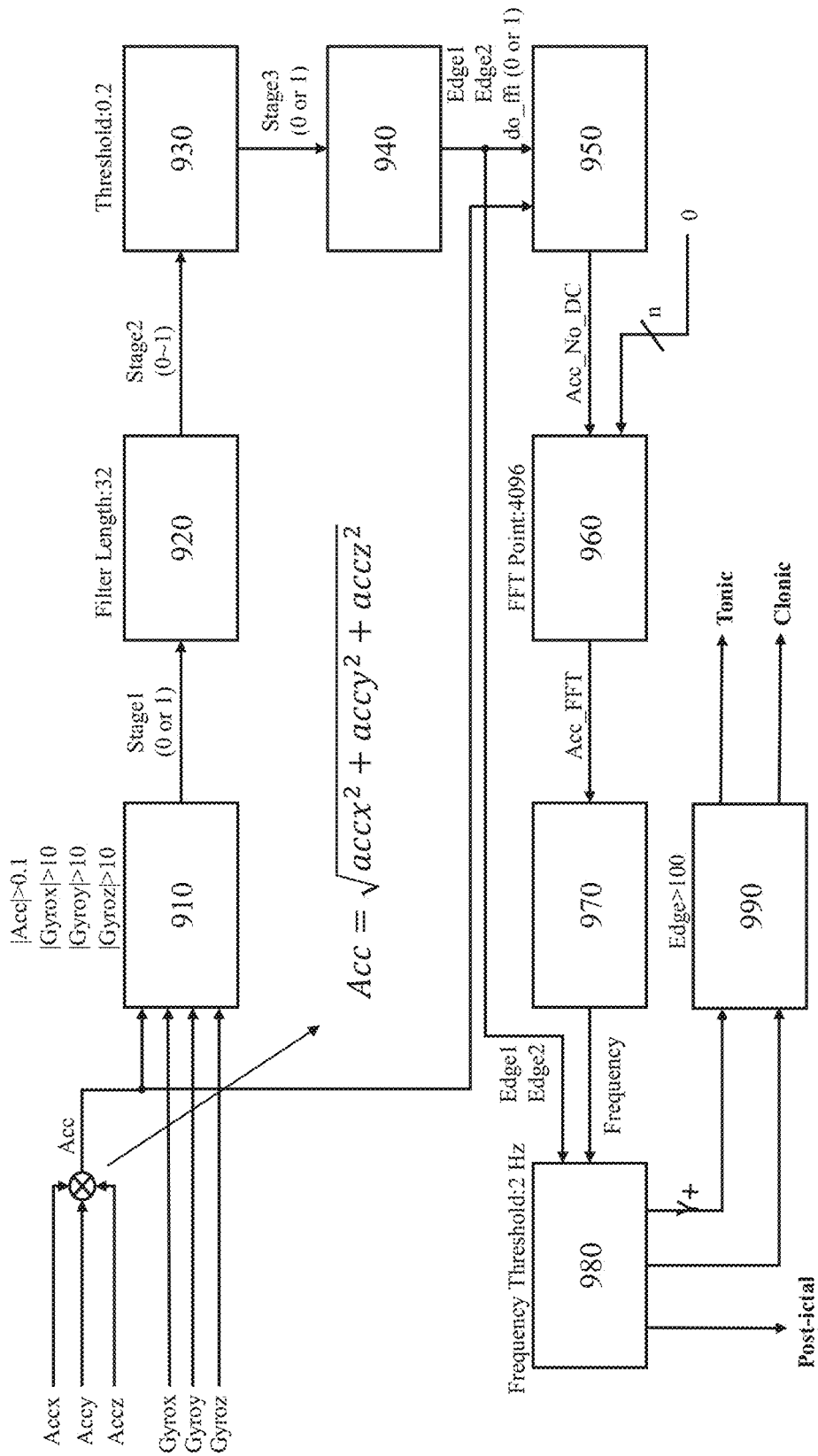
FIG. 9 is a flow chart of a method for detecting epileptic seizures and phases using the system for detection of onset and ictal phases of an epileptic seizure of the present invention.

FIG. 9 is a flow chart of a method for detection of onset and ictal phases of an epileptic seizure useful in the invented system. As shown in the figure, in step 910, the ACC of the three-axis acceleration values and the three-axis angular velocity values, both of the motion sensor are obtained. Compare the reading values with corresponding threshold values, respectively. If a value is higher than the threshold value, it is determined that the extremity where the corresponding motion sensor is worn is in tremor. In step 920, determine whether the tremor amplitude is consistent, and in step 930, determine whether the tremor amplitude exceeds a predetermined value, so as to eliminate possible false alarms. After the above steps, it can be determined that an epilepsy seizure has occurred. Next, in step 940, the clustering edge of the recording waveform is determined, and the start/transition time of the phases of the epileptic seizure is determined accordingly. In step 950, the DC component of the sensed waveform is filtered out and, in step 960, fast Fourier transform is performed on the ACC, followed by in step 970, the peak value of the frequency component is detected. In step 980, determine whether the epilepsy is in seizure. If not, it is determined as the post-seizure phase; otherwise, pulse shaping is performed in step 990, and according to the result, determine as the tonic phase or the clonic phase.

Figure 10:
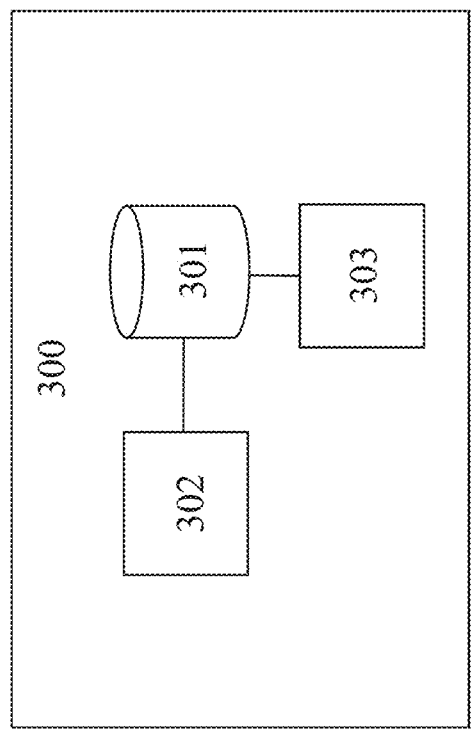
FIG. 10 shows a block diagram of a sensing data interpretation device applicable to the present invention.

From the above tests and description, it is appreciated that the sensing data interpretation device 300 of the present invention serves to automatically marking features in individual sensed result files. FIG. 10 shows a block diagram of a sensing data interpretation device 300 applicable to the present invention. As shown in the figure, the sensing data interpretation device 300 of this invention is equipped with a memory device 301 for storing the sensing data generated by the at least one motion sensor 101-105. The sensing data interpretation device 300 also includes at least one functional module 302 for installing at least one sensing data interpretation program. Each sensing data interpretation program provides at least one interpretation function when in operation, and each is configured to manually or automatically mark a feature to the sensing data in process. The marks that the sensing data interpretation device 300 can automatically generate include: marks representing a feature, reference information, such as: the beginning and the end of an epileptic seizure; an ictal phase of the epileptic seizure, the transition of a phase of the epileptic seizure; or related descriptive information, such as sensor position and sensing time. The reference to be marked may include an event of falling down, raising up etc.

According to this invention, after a sensing data interpretation program installed in the functional module 302 is executed, it can mark features on a sensing data file. The feature may be a phase of an epileptic seizure and its start, end and transition times. Here, the term "phase" pertains to one of the phases of an epileptic seizure, including a preictal phase, onset, a tonic phase, a clonic phase and a postictal phase. The sensing data interpretation program can also normalize the sensing data.

For example, the sensing data interpretation device 300 may be equipped with a human-machine interface 303. After the motion sensing data interpretation program is executed in the functional module 302, the contents of more than one sensing data file can be displayed on the man-machine interface 303 in a predetermined format for the user to manually mark features and/or references. In most preferred embodiments of the present invention, the sensing data interpretation program can automatically mark features and/or reference tags, after it is executed in the function module 302. For example, the start and end times of an epileptic seizure, the start, transition and end times of the ictal phases, they can be identified using the pattern recognition technology based on the tremor amplitude of the extremity, as sensed by the motion sensing devices. The transition of each phase can be judged according to the frequency and amplitude of ACC. In this way, the occurrence and the phases of an epileptic seizure can be identified correctly. The sensing data file after marking becomes a seizure and history record file and provides useful information for the detection, monitoring, recording, judgment, and phase determination of epilepsy. The interpreted and marked sensing data file is stored back to the memory device 301 and can be displayed on the man-machine interface 303.

After sensing data interpretation program in the function module 302 is executed, it can automatically mark the sensing time in any sensing data file. After a sensing data interpretation program in the function module 302 is executed, the sensing data of any sensing data file can be automatically normalized. Regarding the marking of the sensing time, it is already known to those having ordinary skills in the art. In addition, the formalization of the sensing data can be achieved by a skilled person, using the suited statistic theories or according to their experiences, depending on the different sensing devices, objects of the process. For example, the offsets shown in FIG. 6 and FIG. 7 can be corrected by those having ordinary skills in the art. Detailed description thereof are thus omitted. After the time-marking or normalization is completed, the marking or normalization result is recorded in the biomechanical data file and stored back to the memory device 301.

In a preferred embodiment of the present invention, the sensing data interpretation device 300 is configured to recognize at least one synchronization feature in a plurality of sensing data files, and mark a start and/or end time of display for each file, the transition frequency of the displayed content, including the data transition frequency and the frame change frequency along the time axis, according to the synchronization feature. In application, the synchronization feature is preferably a time feature. According to the same or corresponding reference time, multiple sensing results obtained from different sensors or at different times and places are displayed on the same display screen in the same or different formats, making interpretation easier for professionals.

The features marking, information marking, normalization and visualization as described above can be processed without the need of a fixed processing sequence, and there are no certain steps that must be completed. There is no general rule to determine the level of detail for the phase detection of an epileptic seizure or its transition of a sensing data file. Most importantly, the present invention provides a novel system for detection of onset and ictal phases of an epileptic seizure, which can correctly detect the start, transition and end times of an epileptic seizure or its phases, using only the simplest form of a motion sensor. The invention can automatically mark features and references in the sensing data, and converts the sensing data that do not have reference value into valuable information, useful for diagnosis, treatment and rehabilitation. As a result, a system for detection of onset and ictal phases of an epileptic seizure only uses simple sensing devices, and do not require complex or wired sensing equipment, so they can be worn for a long time and can collect sensing data continuously for diagnosis purposes. The present invention further provides a platform for detection of onset and ictal phases of an epileptic seizure to provide services for a great number of professionals and patients.

What is claimed is:

1. A system for detection of onset and ictal phases of an epileptic seizure, comprising at least one motion sensor, at least one intermediate device and a sensing data interpretation device,
   wherein the at least one motion sensor is communicatively connected to the sensing data interpretation device via at least one intermediate device;
   wherein the motion sensor comprises at least one three-axis inertial sensor for sensing the movement of the motion sensor and outputting sensing data; an interface device for receiving user input for setting at least one format for output data of the motion sensor; a wireless communication configured to transmit the sensing data to the at least one intermediate device for exchange of data; and a power supply for supplying electric power to the inertial sensor, the interface device and the wireless communication device;
   wherein the intermediate device is a computer device equipped with a wireless communication function, to establish a communication channel with at least one motion sensor for exchange of data;
   wherein the intermediate device is configured to transmit the sensing data of the at least one motion sensor to the sensing data interpretation device;
   wherein the sensing data interpretation device is provided with a memory device for storing the sensing data generated by the at least one motion sensor;
   wherein the sensing data interpretation device is provided with an application program for detection of onset and ictal phases of an epileptic seizure, configured to perform at least one of the following functions on the sensing data, after being executed in the sensing data interpretation device: marking a feature, marking reference, including an ictal phase of an epileptic seizure, sensor position, sensing time; and normalization;
   wherein the system further comprises a display device for retrieving one or more sensing data file from the memory device of the sensing data interpretation device according to a user's instruction, and displaying the requested data in a format and form specified by the user; and
   wherein the sensing data interpretation device is further configured to recognize at least one synchronization feature in the one or more sensing data file, and determine for each file a start time and/or end time of displaying, as well as a timing of change of display content, including a data transition frequency and a frame change frequency along the time axis, according to the synchronization feature.

2. The system according to claim 1, wherein the application program is configured to, after execution in the sensing data interpretation device, mark a feature on a sensing data file; wherein the feature comprises at least one of the followings: a beginning and end of an epileptic seizure; an ictal phase of the epileptic seizure, a transition of a phase of the epileptic seizure; and related descriptive information.

3. The system according to claim 2, wherein the related descriptive information comprises one of falling down and raising up.

4. The system according to claim 2, wherein the phase comprises one of the following phases of an epileptic seizure: a preictal phase, onset, a tonic phase, a clonic phase and a postictal phase.

5. The system according to claim 2, wherein the application program is further configured to mark a sensing time on a sensing data file.

6. The system according to claim 2, wherein the application program is further configured to normalize sensing data of a sensing data file.

7. The system according to claim 1, wherein the three-axis inertial sensor comprises an accelerometer.

8. The system according to claim 7, wherein the motion sensor further comprises a gyroscope and/or a magnetometer.

9. The system according to claim 8, wherein the motion sensor further comprises a memory device for storage of sensing data of the inertial sensor, the gyroscope and/or the magnetometer.

10. The system according to claim 9, wherein the motion sensor is configured to continuously store the sensing data in the memory device in the at least one format for a predetermined time.

11. The system according to claim 1, wherein the motion sensor is configured to continuously output the sensing data via the wireless communication device in the at least one format for a predetermined time.

12. The system according to claim 1, wherein the interface device of the motion sensor is built in the intermediate device.

13. The system according to claim 12, wherein the intermediate device provides a graphical setting interface, for a user to input setting parameters, and to provide the parameters to the motion sensor to change a format of output sensing data of the motion sensor.

14. The system according to claim 13, wherein the intermediate device is a smart phone.

15. The system according to claim 4, wherein the interface device of the motion sensor is built in the intermediate device.

16. The system according to claim 15, wherein the intermediate device provides a graphical setting interface, for a user to input setting parameters, and to provide the parameters to the motion sensor to change a format of output sensing data of the motion sensor.

17. The system according to claim 16, wherein the intermediate device is a smart phone.

18. The system according to claim 1, wherein the sensing data interpretation device is built in the intermediate device, in form of application software.

19. The system according to claim 18, wherein the intermediate device is a smart phone.

20. The system according to claim 4, wherein the sensing data interpretation device is built in the intermediate device, in form of application software.

21. The system according to claim 20, wherein the intermediate device is a smart phone.

22. The system according to claim 1, wherein the sensing data interpretation device is built in a server computer connected to the Internet in form of application software, to form a platform, wherein the platform is configured to communicate with a plurality of motion sensors for uploading sensing data thereto via one of a plurality of intermediate device, and to communicate with computer devices in connection with the server computer, for utilization of the sensing data stored therein, including at least one of processing the sensing data and downloading a processing result.

23. The system according to claim 4, wherein the sensing data interpretation device is built in a server computer to form an epileptic seizure detection platform, which serves to communicate with a plurality of motion sensors for uploading sensing data thereto via one of a plurality of intermediate device, and to communicate with computer devices in connection with the server computer, for utilization of the sensing data stored therein, including at least one of processing the sensing data and downloading a processing result.

* * * * *